United States Patent
Grez et al.

(10) Patent No.: US 6,739,012 B2
(45) Date of Patent: May 25, 2004

(54) POWER TOOTHBRUSH WITH BRUSHING PRESSURE FEEDBACK

(75) Inventors: Joseph W. Grez, Snoqualmie, WA (US); Duane B. Kutsch, Seattle, WA (US); Bruce E Taber, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 288 days.

(21) Appl. No.: 10/029,309

(22) Filed: Dec. 20, 2001

(65) Prior Publication Data
US 2003/0115693 A1 Jun. 26, 2003

(51) Int. Cl.[7] .......................... A46B 13/02; A46B 15/00
(52) U.S. Cl. .......................... 15/22.1; 15/22.2; 318/119
(58) Field of Search ................. 15/22.1, 22.2, 15/22.4, 28; 310/17, 20, 81; 318/114, 119, 126–131

(56) References Cited

U.S. PATENT DOCUMENTS

| | | | |
|---|---|---|---|
| 5,617,601 A | * 4/1997 | McDougall | 15/22.1 |
| 5,732,432 A | * 3/1998 | Hui | 15/22.1 |
| 5,815,872 A | * 10/1998 | Meginniss et al. | 15/22.1 |
| 6,140,723 A | * 10/2000 | Matsui et al. | 310/81 |
| 6,588,042 B2 | * 7/2003 | Fritsch et al. | 15/22.1 |

\* cited by examiner

*Primary Examiner*—Mark Spisich
*Assistant Examiner*—Shay L Balsis
(74) *Attorney, Agent, or Firm*—Ernestine C. Bartlett

(57) ABSTRACT

The vibrating toothbrush includes a first arm portion with a brushhead mounted at a free end and a second arm portion joined by a hinge-like portion. The first and second arm portions have first and second natural resonant frequencies. A spring member connects the second arm portion to the first arm portion, and a solenoid actuator is also connected between the first and second arm portions. A contact switch assembly is responsive to a DC battery voltage such that when the switch is closed, the first arm portion is drawn in one direction by the actuator, which results in compression of the spring and opening of the switch, with the compressed spring moving the first arm portion in the opposing direction until the switch again closes, so that the brushhead moves back and forth with the opening and closing of the switch. A pressure feedback arrangement makes use of the spring element and a nodal mount which extends from the spring at a selected point therealong to the handle of the toothbrush. The first and second natural resonant frequencies are selected such that when the brushhead is loaded with a selected amount of pressure, there is substantially no vibration transmitted to the handle.

14 Claims, 1 Drawing Sheet

POWER TOOTHBRUSH WITH BRUSHING PRESSURE FEEDBACK

TECHNICAL FIELD

This invention relates to a resonant vibrating power toothbrush having first and second vibrating members joined by a hinge portion and a spring and driven by an actuating member, and also concerns a power toothbrush having a brushing pressure feedback capability.

BACKGROUND OF THE INVENTION

A wide variety of power toothbrushes, using various driving arrangements, are well known. Power toothbrushes generally provide a better and more reliable cleaning action than manual toothbrushes and accordingly are generally preferable in order to maintain good dental hygiene. Many of these toothbrushes are powered by a self-contained DC battery. The driving arrangements include various motors which produce a variety of brushhead motions, including rotary and back-and-forth actions, as well as other arrangements using magnetic drivers.

The frequency of the brushhead action of these toothbrushes varies considerably, typically from a few Hertz to several thousand Hertz and, in some cases, ultrasonic frequencies. Many of these power toothbrushes, however, are expensive and at least in some cases are quite complex in design and operation. The expense and complexity of such power toothbrushes preclude a particular class of customers from receiving the cleaning benefits of a reliable power toothbrush. Hence, it would be desirable to have a power toothbrush which has a frequency and amplitude of motion which is effective in cleaning teeth, but is also inexpensive to produce and reliable in operation.

One important operational feature of a power toothbrush is the brushing pressure applied to the teeth. Proper brushing pressure has been discovered to be important in terms of achieving a desired cleansing effect, but care must be taken to not apply too much pressure, which may damage gums and other tissue or too little pressure, which would not be effective in cleaning. Numerous attempts have been made to produce accurate brushing pressure information with an indicator which can readily communicate to the user that the brushing pressure is either within a desired range or too high or too low. However, the known brushing pressure indicator systems are often quite complex, expensive and unreliable. Hence, it would also be desirable to have a reliable and inexpensive brushing pressure indicator for a power toothbrush.

DISCLOSURE OF THE INVENTION

A first aspect of the present invention is a vibrating toothbrush which has a handle portion, comprising: a first vibrating arm portion, having a brushhead mounted at a free end portion thereof; a second vibrating arm portion, connected to an opposing end of the first arm portion by a hinge acting connecting element, wherein the first and second arm portions have first and second natural resonant frequencies; a spring member connecting the second arm portion in the vicinity of a free end thereof to the first arm portion; an actuator connected between the first and second arm portions; and a switch element for selectively applying a DC voltage to the actuator, wherein in operation, when the switch is closed, the first arm portion is drawn toward the second arm portion by the actuator, which compresses the spring element and opens the switch element, and wherein return action of the spring when the switch element is open moves the first arm portion away from the second arm portion to the point where the switch again closes, resulting in a back-and-forth movement of the brushhead.

A second aspect of the invention is a vibrating toothbrush which includes a pressure feedback capability, comprising: an arm portion on which is mounted a brushhead at a free end thereof; a driving assembly for moving the arm portion and hence the brushhead in a manner to clean teeth; a spring element connected between the driver assembly and the arm portion; and a nodal mount connecting the spring element to the handle at a preselected position therealong, wherein the preselected position is such that when the brushhead is loaded with a preselected correct amount of brushing pressure, vibration to the handle through the nodal mount is significantly reduced, indicating to the user that a correct brushing pressure is being used.

BEST MODE FOR CARRYING OUT THE INVENTION

Figure 1:
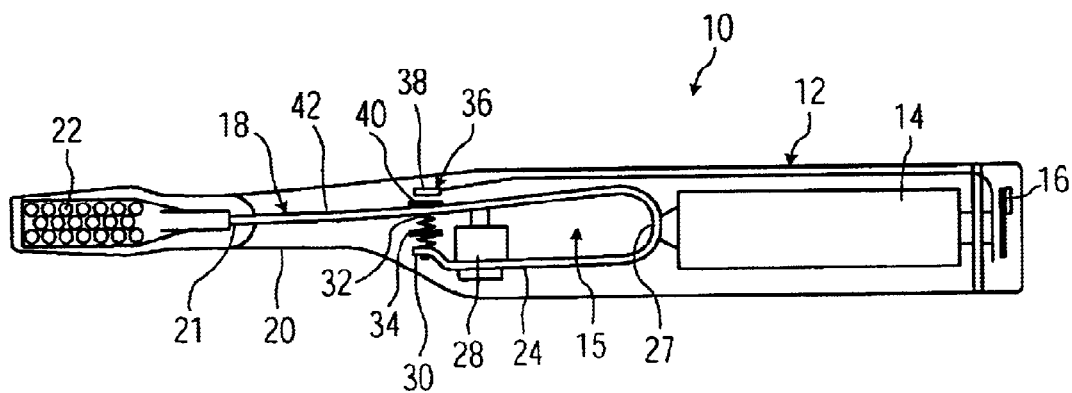
FIG. 1 is an elevational view showing the toothbrush of the present invention, embodying a low cost power toothbrush arrangement in combination with a brushing pressure indicator mechanism.

FIG. 1 shows the toothbrush of the present invention. It includes a low cost resonant vibrating toothbrush design, but also includes a structure for providing an indication to the user of brushing pressure. The toothbrush, shown generally at 10, includes a handle portion 12 within which is positioned a battery 14 which supplies power to the toothbrush and an on/off switch 16. These elements are shown in general form, as they can take many different configurations and arrangements. Inside of handle 12, a two-part vibrating element assembly 15 is mounted. The two-part vibrating element assembly 15 includes a first vibrating portion 18, which is elongated and extends through a neck portion 20 of handle 12. Mounted on a free end 21 of the first vibrating portion 18 is a brushhead which includes a conventional set of toothbrush bristles 22.

The vibrating element assembly 15 also includes a second vibrating portion 24, which is spaced a short distance laterally from first vibrating portion 18, although considerably shorter and contained entirely within handle 12. The first and second vibrating portions 18 and 24 are joined by a hinge portion 27 within the handle 12. In the embodiment shown, the first and second vibrating portions 18 and 24 and hinge portion 27 are one continuous element between free end 21 of the first vibrating portion and free end 30 of the second vibrating portion. It should be understood, however, that the three portions could be individual elements joined together.

The first vibrating portion 18, in operation, moves or vibrates independently of second vibrating portion 24 about hinge portion 27. Connected to and extending between the first and second vibrating portions within handle 12, and positioned close to the free end 30 of second vibrating portion 24, is a conventional solenoid 28. A body portion of solenoid 28 is secured to the second vibrating portion 24, while a plunger portion is secured to the first vibrating portion 18, as shown in FIG. 1.

Also extending between the first vibrating portion 18 and the second vibrating portion 24, at the free end 30 of the second vibrating portion, is a spring element 32. A mounting member 34, referred to also as a nodal mount, is connected between spring element 32 and handle 12. Spring element 32 can be a single spring or two springs separated by mounting element 34.

The toothbrush 10 also includes a contact switch assembly 36. The switch assembly 36 includes a first contact portion 38 which is electrically connected to one side of battery 14 and includes a lead portion which is mounted to the inside surface of the handle and a second contact portion 40 which is mounted on the outer surface 42 of the first vibrating portion 18.

Figure 2:
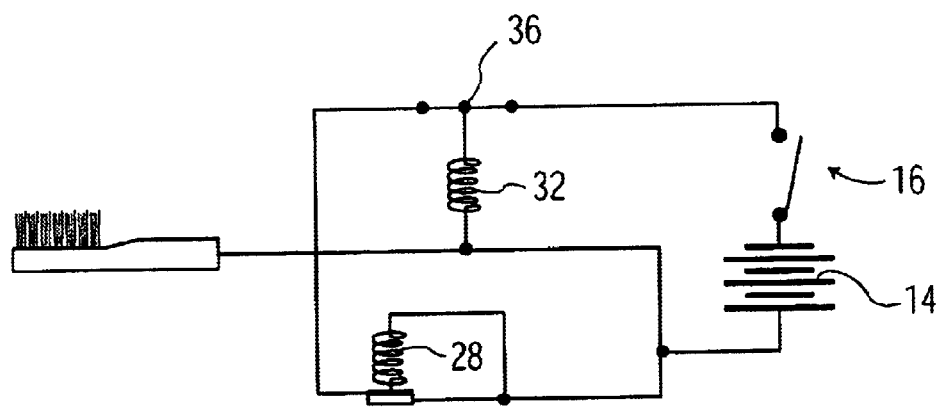
FIG. 2 is a simplified electrical diagram for the toothbrush of FIG. 1.

FIG. 2 shows a simplified electrical connection diagram corresponding to the above description. Battery 14 and the on/off switch 16 are contained within the handle 12. One side of the battery is connected to the coil in solenoid 28 (as well as the vibrating element assembly 15), while the other side of the battery is connected to one side of the on/off switch 16. The other side of the on/off switch 16 is connected to contact portion 38 of switch 36, with contact portion 40 of the switch being connected to the plunger portion of the solenoid when switch 36 is closed. The spring 32 is shown connected between the contact switch 36 and the vibrating element assembly when the switch 36 is in a closed position.

In operation, beginning when contact switch 36 is in its closed position, the electrical circuit with battery 14 is closed. The closed circuit activates solenoid 28, which pulls the first vibrating portion 18 toward the second vibrating portion 24, by virtue of the action of plunger 28. This results in a movement of the brushhead in one direction (down in FIG. 1) and also results in contact switch 36 opening and spring element 32 compressing. The electrical circuit is now open, so that the plunger portion of the solenoid can no longer pull on the first vibrating portion 18. The energy stored in the compressed spring element 32 releases and the first vibrating portion moves, under the urging of spring 32, in an opposing direction (upwardly in FIG. 1). Switch 36 thus alternately makes and breaks contact, leading to a back-and-forth (up/down in FIG. 1) movement of the brushhead, at a natural resonant frequency which is the average of the natural resonant frequencies of the first and second vibrating portions, and their associated portions of spring 32. The structure of FIG. 1 thus produces a reliable low-cost vibrating movement of the brushhead at a selected frequency.

The first vibrating portion 18 is arranged and configured to have a first selected natural resonant frequency, while the second vibrating portion 24 has a second selected natural resonant frequency. In another aspect of the present invention the second natural resonant frequency is slightly greater or slightly less than the first natural resonant frequency, e.g. 5 Hz in the embodiment shown, although the difference in frequency can vary to some extent. A change of mass of either vibrating portion or a change in the spring characteristic from the nodal mount 34 to the respective vibrating portions will change the resonant frequency of that portion of the system. Typically, the contribution of the spring will be the same to each vibrating portion, because the characteristics of each part will be the same.

If the first vibrating portion 18 is "loaded", such as by use of the toothbrush in brushing, against the teeth, the resonant frequency of the first vibrating portion will increase (or in some cases decrease) slightly. The resonant frequency of the second vibrating portion, however, will remain the same. Since specific brushing pressure has a known effect on the first natural resonant frequency, then the frequency difference between the first and second natural resonant frequencies can be selected so that when the brush is properly loaded (with proper brushing pressure), the first and second natural resonant frequencies will be equal. The position of the nodal mount, furthermore, is selected so that when the first and second natural resonant frequencies are identical, there will be a null at the nodal mount 34 and, hence, little or no vibration will be transmitted to the handle. This lack of vibration at a specific proper value of brushing pressure is a good feedback indication to the user of when proper brushing pressure is being applied.

Thus, when the correct amount of pressure is being applied to the teeth by a user, the natural resonant frequency of the first vibrating portion will change to match exactly the natural resonant frequency of the second vibrating portion, which in turn results in a vibration "null" at the nodal mount, which "null" (no vibration) in turn is readily noticeable to the user. When the brushing pressure is incorrect, either too high or too low, the first natural resonant frequency will not match the second natural resonant frequency (they will be off by some value of frequency) and vibration will be coupled to the handle through the nodal mount. This alerts the user to the fact that incorrect brushing pressure is being used.

Accordingly, a toothbrush has been described, which in one aspect is a reliable, inexpensive vibrating power toothbrush. In another aspect of the invention, feedback is provided to the user via a nodal mount arrangement to indicate proper (or improper) brushing pressure.

Relative to possible alternatives to selected portions of the preferred embodiment, it should be understood that, with respect to the brushing pressure feedback feature, the nodal mount arrangement shown can be used with toothbrush structures different than that shown in FIG. 1. For instance, the toothbrush may have a motor which directly drives a linear spring arrangement with a nodal mount at a selected point therealong. Brushing pressure, again, will change the natural resonant frequency of the drive assembly from the spring out to the brushhead. When the natural resonant frequency matches the drive frequency of the motor, a null point will result, which if coincident with the mounting point for the spring, will result in a null in vibration to the handle, thus signaling to the user that a proper brushing pressure is being used. The brushing pressure feedback concept disclosed herein, using a spring-based nodal mount arrangement, thus can be used with a variety of drive configurations.

Also, it should be understood that there are alternatives to various portions of the system shown in FIG. 1. For instance, the contacts of switch 36 could be entirely mounted on the first vibrating portion, with the contacts opening and closing upon acceleration of the arm instead of the arm's position. The switch 36 also could be a solid-state switch or an accelerometer. Also, as indicated briefly above, instead of a solenoid coil-type actuator, a permanent magnet actuator or a piezoelectric or double-coil actuator could be used. Various spring devices could also be used for spring element 32, including coil springs, leaf springs, magnetic, elastomeric, Belleville-washer or other similar spring devices. The hinge portion could also be changed, to comprise a separate hinge portion connected to two vibrating portions. A plastic clamp or a pin hinge or a movable interlocking element for the two vibrating arm portions could also be used.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A vibrating power toothbrush having a handle portion, comprising:

a first vibrating arm portion, having a brushhead mounted at a free end portion thereof;

a second vibrating arm portion, connected to an opposing end of the first arm portion by a connecting element, wherein the first and second arm portions have first and second natural resonant frequencies;

a spring member connecting the second arm portion in the vicinity of a free end thereof to the first arm portion;

an actuator connected between the first and second arm portions; and a switch element for selectively applying a DC voltage to the actuator, wherein in operation, when the switch is closed, the first arm portion is drawn toward the second arm portion by the actuator, which compresses the spring member and opens the switch element, and wherein return action of the spring member when the switch element is open moves the first arm portion away from the second arm portion to the point where the switch element again closes, resulting in a back-and-forth movement of the brushhead.

2. A toothbrush of claim 1, wherein the actuator is a solenoid, having a coil portion connected to the second vibrating arm portion and a movable plunger portion connected to the first vibrating arm portion.

3. A toothbrush of claim 1, including a DC battery for supplying said DC voltage.

4. A toothbrush of claim 3, wherein the switch element is a contact switch having a first contact portion connected to the battery and mounted to the handle portion of the toothbrush, and a second contact portion mounted to a surface of the first arm portion.

5. A toothbrush of claim 1, wherein the first arm portion, the second arm portion and the connecting element comprises a single, continuous element, with the connecting element acting as a hinge between the first and second arm portions.

6. A toothbrush of claim 1, including a nodal mount element connecting the spring member at a selected position therealong to the handle portion.

7. A vibrating toothbrush which includes a brushing pressure feedback capability, comprising:

an arm portion on which is mounted a brushhead at a free end thereof;

a driving assembly for moving the arm portion and hence the brushhead in a manner to clean teeth;

a spring element connected between the driving assembly and the arm portion; and a nodal mount connecting the spring element to a handle at a preselected position therealong, wherein the preselected position is such that when the brushhead is loaded with a preselected correct amount of brushing pressure, vibration transmitted to the handle through the nodal mount is significantly reduced, indicating to the user that a correct brushing pressure is being used.

8. A toothbrush of claim 7, wherein the spring element is a coil spring.

9. A toothbrush of claim 7, wherein the spring element is a leaf spring.

10. A toothbrush of claim 7, wherein the nodal mount is a spring mount.

11. A toothbrush of claim 7, wherein the nodal mount is a non-resilient firm mount.

12. A toothbrush of claim 7, wherein the application of brushing pressure to the brushhead against teeth of a user changes the natural resonant frequency of the arm portion so as to shift the point of reduced vibration along the spring element, and wherein when the brushing pressure is correct, the point of reduced vibration is at the nodal mount point.

13. A toothbrush of claim 7, wherein the spring element is one spring.

14. A toothbrush of claim 7, wherein the spring element is two springs, separated by the nodal mount.

* * * * *